US008974813B2

(12) United States Patent
Tuominen et al.

(10) Patent No.: US 8,974,813 B2
(45) Date of Patent: Mar. 10, 2015

(54) HYDROPHILIC POLYURETHANE COMPOSITIONS

(75) Inventors: Jukka Tuominen, Kuusisto (FI); Amaia Zurutuza, Glasgow (GB); Mark Livingstone, Irvine (GB); Janet Anne Halliday, West Lothian (GB)

(73) Assignee: Ferring B.V., Hoofddorp (NL)

( * ) Notice: Subject to any disclaimer, the term of this patent is extended or adjusted under 35 U.S.C. 154(b) by 809 days.

(21) Appl. No.: 12/307,514

(22) PCT Filed: Jun. 27, 2007

(86) PCT No.: PCT/GB2007/002401
§ 371 (c)(1),
(2), (4) Date: Jul. 2, 2009

(87) PCT Pub. No.: WO2008/003932
PCT Pub. Date: Jan. 10, 2008

(65) Prior Publication Data
US 2009/0291120 A1 Nov. 26, 2009

(30) Foreign Application Priority Data

Jul. 5, 2006 (GB) .................... 0613333.4

(51) Int. Cl.
| A61F 6/14 | (2006.01) |
| A61F 13/00 | (2006.01) |
| A61K 47/30 | (2006.01) |
| C08G 18/20 | (2006.01) |
| A61K 9/00 | (2006.01) |
| C08G 18/48 | (2006.01) |
| C08G 18/73 | (2006.01) |
| C08G 18/75 | (2006.01) |
| A61K 47/34 | (2006.01) |

(52) U.S. Cl.
CPC .......... C08G 18/2063 (2013.01); A61K 9/0024 (2013.01); A61K 9/0036 (2013.01); C08G 18/4841 (2013.01); C08G 18/73 (2013.01); C08G 18/758 (2013.01); A61K 47/34 (2013.01)
USPC ........... 424/432; 424/422; 424/435; 424/449; 514/772.7

(58) Field of Classification Search
None
See application file for complete search history.

(56) References Cited

U.S. PATENT DOCUMENTS

| 3,487,068 A | 12/1969 | Morozowich et al. |
| 3,565,991 A | 2/1971 | Short |
| 3,598,122 A | 8/1971 | Zaffaroni |
| 3,598,123 A | 8/1971 | Zaffaroni |
| 3,639,157 A | 2/1972 | Wunder et al. |
| 3,731,683 A | 5/1973 | Zaffaroni |
| 3,734,097 A | 5/1973 | Zaffaroni |
| 3,737,521 A | 6/1973 | Born |
| 3,760,805 A | 9/1973 | Higuchi |
| 3,797,494 A | 3/1974 | Zaffaroni |
| 3,830,907 A | 8/1974 | Short |
| 3,845,761 A | 11/1974 | Zaffaroni |
| 3,845,770 A | 11/1974 | Theeuwes et al. |
| 3,854,480 A | 12/1974 | Zaffaroni |
| 3,860,701 A | 1/1975 | Short |
| 3,867,933 A | 2/1975 | Kitrilakis |
| 3,881,043 A | 4/1975 | Rieser et al. |
| 3,892,842 A | 7/1975 | Zaffaroni |
| 3,896,819 A | 7/1975 | Zaffaroni |
| 3,901,852 A * | 8/1975 | Shah .............................. 528/85 |
| 3,916,898 A | 11/1975 | Robinson |
| 3,916,899 A | 11/1975 | Theeuwes et al. |
| 3,921,636 A | 11/1975 | Zaffaroni |
| 3,931,113 A | 1/1976 | Seeger et al. |
| 3,934,580 A | 1/1976 | Cournut |
| 3,941,880 A | 3/1976 | Short |
| 3,948,254 A | 4/1976 | Zaffaroni |
| 3,948,262 A | 4/1976 | Zaffaroni |
| 3,967,618 A | 7/1976 | Zaffaroni |
| 3,993,072 A | 11/1976 | Zaffaroni |
| 3,993,073 A | 11/1976 | Zaffaroni |
| 3,995,631 A | 12/1976 | Higuchi et al. |
| 4,018,918 A | 4/1977 | Ayer et al. |
| 4,034,756 A | 7/1977 | Higuchi et al. |
| 4,036,227 A | 7/1977 | Zaffaroni et al. |
| 4,041,208 A | 8/1977 | Seeger et al. |
| 4,093,708 A | 6/1978 | Zaffaroni et al. |
| 4,096,238 A | 6/1978 | Zaffaroni et al. |
| 4,098,747 A | 7/1978 | Bailey et al. |
| 4,135,514 A | 1/1979 | Zaffaroni et al. |
| 4,142,526 A | 3/1979 | Zaffaroni et al. |

(Continued)

FOREIGN PATENT DOCUMENTS

| DE | 19842636 A1 | 3/1999 |
| DE | 19742217 | 4/1999 |

(Continued)

OTHER PUBLICATIONS

PCT/GB2007/002401 International Search Report dated Oct. 24, 2007.

(Continued)

Primary Examiner — Kortney L Kinkel
Assistant Examiner — Melissa Javier
(74) Attorney, Agent, or Firm — Fish & Richardson P.C.

(57) ABSTRACT

A water-swellable linear polymer is made by reacting together a polyethylene oxide of number average molecular weight less than 4,000, an aliphatic diol, and a difunctional diisocyanate. Controlled release composition comprises the polymer together with an active agent. The polymer is able to take up pharmaceutically active agents of molecular weight 200 to 20,000.

12 Claims, 1 Drawing Sheet

(56) References Cited

U.S. PATENT DOCUMENTS

| | | |
|---|---|---|
| 4,202,880 A | 5/1980 | Fildes et al. |
| 4,205,115 A | 5/1980 | Piccirilli et al. |
| 4,215,691 A | 8/1980 | Wong |
| 4,235,988 A * | 11/1980 | Fildes et al. ............... 514/772.1 |
| 4,237,885 A | 12/1980 | Wong |
| 4,250,611 A | 2/1981 | Wong |
| 4,264,757 A | 4/1981 | Park |
| 4,276,405 A | 6/1981 | Koleske et al. |
| 4,286,587 A | 9/1981 | Wong |
| 4,289,757 A | 9/1981 | Glenn |
| 4,327,727 A | 5/1982 | Prahl et al. |
| 4,379,915 A | 4/1983 | Watanabe et al. |
| 4,402,695 A | 9/1983 | Wong |
| 4,404,296 A | 9/1983 | Schäpel |
| 4,426,485 A | 1/1984 | Hoy et al. |
| 4,438,225 A | 3/1984 | Peerman |
| 4,447,591 A | 5/1984 | Watanabe et al. |
| 4,466,936 A | 8/1984 | Schäpel |
| 4,503,216 A | 3/1985 | Fagerburg et al. |
| 4,568,741 A | 2/1986 | Livingston |
| 4,594,240 A | 6/1986 | Kawata et al. |
| 4,596,576 A | 6/1986 | de Nijs |
| 4,647,596 A | 3/1987 | Ishii et al. |
| 4,694,238 A | 9/1987 | Norton |
| 4,707,495 A | 11/1987 | Rosenthale et al. |
| 4,731,289 A | 3/1988 | Coleman |
| 4,767,787 A | 8/1988 | Kawata et al. |
| 4,804,691 A | 2/1989 | English et al. |
| 4,814,182 A | 3/1989 | Graham et al. |
| 4,818,517 A | 4/1989 | Kwee et al. |
| 4,894,238 A | 1/1990 | Embry et al. |
| 4,895,934 A | 1/1990 | Matier et al. |
| 4,917,686 A | 4/1990 | Bayston et al. |
| 4,931,288 A | 6/1990 | Embrey et al. |
| 4,933,418 A | 6/1990 | Sterrett |
| 4,940,588 A | 7/1990 | Sparks et al. |
| 4,945,149 A | 7/1990 | Matsumoto et al. |
| 4,952,402 A | 8/1990 | Sparks et al. |
| 4,954,043 A | 9/1990 | Yoshida et al. |
| 4,973,304 A | 11/1990 | Graham et al. |
| 5,000,955 A | 3/1991 | Gould |
| 5,002,540 A | 3/1991 | Brodman et al. |
| 5,017,382 A | 5/1991 | Embrey et al. |
| 5,023,252 A | 6/1991 | Hseih |
| 5,035,891 A | 7/1991 | Runkel et al. |
| 5,045,622 A | 9/1991 | Kohno et al. |
| 5,049,638 A | 9/1991 | Matsumoto et al. |
| 5,055,516 A | 10/1991 | Fisch et al. |
| 5,057,573 A | 10/1991 | Pascault et al. |
| 5,061,254 A | 10/1991 | Karakelle et al. |
| 5,079,009 A | 1/1992 | Embrey et al. |
| 5,100,926 A | 3/1992 | Kondo et al. |
| 5,110,598 A | 5/1992 | Kwan |
| 5,114,718 A | 5/1992 | Damani |
| 5,116,932 A | 5/1992 | Fujiwa |
| 5,118,779 A | 6/1992 | Szycher |
| 5,130,126 A | 7/1992 | Koyama et al. |
| 5,134,151 A | 7/1992 | Bartroli et al. |
| 5,156,900 A | 10/1992 | Nishimura |
| 5,159,047 A | 10/1992 | Simms |
| 5,176,907 A | 1/1993 | Leong |
| 5,178,874 A | 1/1993 | Kwan et al. |
| 5,219,663 A | 6/1993 | Kohno et al. |
| 5,219,885 A | 6/1993 | Frolich et al. |
| 5,252,602 A | 10/1993 | Alam et al. |
| 5,269,321 A | 12/1993 | MacDonald et al. |
| 5,283,297 A | 2/1994 | Miyachi et al. |
| 5,310,759 A | 5/1994 | Bockman |
| 5,312,865 A | 5/1994 | Hoefer et al. |
| 5,322,063 A | 6/1994 | Allen et al. |
| 5,324,746 A | 6/1994 | McKee et al. |
| 5,326,632 A | 7/1994 | Zenda et al. |
| 5,328,954 A | 7/1994 | Sarangapani |
| 5,354,556 A | 10/1994 | Sparks et al. |
| 5,374,704 A | 12/1994 | Muller et al. |
| 5,464,868 A | 11/1995 | Frolich et al. |
| 5,470,829 A | 11/1995 | Prisell et al. |
| 5,472,785 A | 12/1995 | Stobbie, IV et al. |
| 5,474,767 A | 12/1995 | Tremont |
| 5,505,962 A | 4/1996 | Sparks |
| 5,510,384 A | 4/1996 | McKee et al. |
| 5,514,698 A | 5/1996 | Ahmad et al. |
| 5,527,534 A | 6/1996 | Myhling |
| 5,574,102 A | 11/1996 | Tanigami et al. |
| 5,578,640 A | 11/1996 | Hanson |
| 5,578,643 A | 11/1996 | Hanson |
| 5,605,931 A | 2/1997 | Hanson |
| 5,627,254 A | 5/1997 | Oriani |
| 5,634,895 A | 6/1997 | Igo et al. |
| 5,650,171 A | 7/1997 | Quigley, Jr. et al. |
| 5,652,274 A | 7/1997 | Martin |
| 5,659,003 A | 8/1997 | Menovcik et al. |
| 5,676,939 A | 10/1997 | Tremont |
| 5,681,278 A | 10/1997 | Igo et al. |
| 5,681,850 A | 10/1997 | Frolich et al. |
| 5,686,425 A | 11/1997 | Lee |
| 5,693,319 A | 12/1997 | Tremont |
| 5,700,483 A | 12/1997 | Quigley, Jr. et al. |
| 5,710,215 A | 1/1998 | Abend |
| 5,716,676 A | 2/1998 | Schutze et al. |
| 5,723,552 A | 3/1998 | Menovcik et al. |
| 5,726,244 A | 3/1998 | McGee et al. |
| 5,726,274 A | 3/1998 | Menovcik et al. |
| 5,731,303 A | 3/1998 | Hsieh |
| 5,733,538 A | 3/1998 | Riffle |
| 5,739,113 A | 4/1998 | Lee |
| 5,744,550 A | 4/1998 | Menovcik et al. |
| 5,747,058 A | 5/1998 | Tipton et al. |
| 5,747,582 A | 5/1998 | Schutze et al. |
| 5,760,127 A | 6/1998 | Bammel et al. |
| 5,763,399 A | 6/1998 | Lee |
| 5,770,650 A | 6/1998 | McGee et al. |
| 5,777,048 A | 7/1998 | Ohrbom et al. |
| 5,780,049 A | 7/1998 | Deckner et al. |
| 5,792,810 A | 8/1998 | Menovcik et al. |
| 5,795,567 A | 8/1998 | Tremont |
| 5,817,343 A | 10/1998 | Burke |
| 5,827,925 A | 10/1998 | Tremont et al. |
| 5,827,930 A | 10/1998 | Ohrbom et al. |
| 5,827,931 A | 10/1998 | Menovcik et al. |
| 5,843,961 A | 12/1998 | Kock et al. |
| 5,849,803 A | 12/1998 | Kock et al. |
| 5,853,767 A | 12/1998 | Melman |
| 5,854,385 A | 12/1998 | McGee et al. |
| 5,855,906 A | 1/1999 | McClay |
| 5,872,195 A | 2/1999 | Green et al. |
| 5,877,216 A | 3/1999 | Place et al. |
| 5,886,039 A | 3/1999 | Kock et al. |
| 5,888,930 A | 3/1999 | Smith et al. |
| 5,891,915 A | 4/1999 | Wysor et al. |
| 5,897,879 A | 4/1999 | Friedman et al. |
| 5,900,433 A | 5/1999 | Igo et al. |
| 5,935,939 A | 8/1999 | Kararli et al. |
| 5,942,512 A | 8/1999 | Kock et al. |
| 5,942,545 A | 8/1999 | Samour et al. |
| 5,948,416 A | 9/1999 | Wagner et al. |
| 5,959,775 A | 9/1999 | Joseph et al. |
| 5,965,662 A | 10/1999 | Krebs et al. |
| 5,968,542 A | 10/1999 | Tipton |
| 5,972,372 A | 10/1999 | Saleh et al. |
| 5,973,002 A | 10/1999 | Frolich et al. |
| 5,977,172 A | 11/1999 | Yoshikawa et al. |
| 5,985,859 A | 11/1999 | Luo |
| 5,994,479 A | 11/1999 | Green et al. |
| 5,994,492 A | 11/1999 | Graham et al. |
| 6,008,312 A | 12/1999 | Shirasaka |
| 6,013,637 A | 1/2000 | Klein et al. |
| 6,022,554 A | 2/2000 | Lee et al. |
| 6,028,057 A | 2/2000 | Burns |
| 6,031,002 A | 2/2000 | Wysor et al. |
| 6,039,968 A | 3/2000 | Nabahi |
| 6,040,062 A | 3/2000 | McGee et al. |
| 6,043,224 A | 3/2000 | Lee et al. |
| 6,046,244 A | 4/2000 | Buyuktimkin et al. |

(56) References Cited

U.S. PATENT DOCUMENTS

| | | |
|---|---|---|
| 6,080,825 A | 6/2000 | Ohrbom et al. |
| 6,084,038 A | 7/2000 | Ohrbom et al. |
| 6,086,909 A | 7/2000 | Harrison et al. |
| 6,093,270 A | 7/2000 | Ferencz et al. |
| 6,103,256 A | 8/2000 | Nabahi |
| 6,103,765 A | 8/2000 | Neal |
| 6,103,852 A | 8/2000 | Shirasaka |
| 6,114,444 A | 9/2000 | Rehfuss et al. |
| 6,117,024 A | 9/2000 | Dewanjee |
| 6,117,843 A | 9/2000 | Baroody et al. |
| 6,123,963 A | 9/2000 | Kim et al. |
| 6,126,958 A | 10/2000 | Saleh et al. |
| 6,130,200 A | 10/2000 | Brodbeck et al. |
| 6,130,309 A | 10/2000 | Reich et al. |
| 6,140,453 A | 10/2000 | Barges et al. |
| 6,150,489 A | 11/2000 | Pudleiner et al. |
| 6,160,058 A | 12/2000 | Ohrbom et al. |
| 6,184,248 B1 | 2/2001 | Lee et al. |
| 6,187,756 B1 | 2/2001 | Lee et al. |
| 6,188,039 B1 | 2/2001 | Gass |
| 6,197,327 B1 | 3/2001 | Harrison et al. |
| 6,210,343 B1 | 4/2001 | Kanakaris et al. |
| 6,210,441 B1 | 4/2001 | Flodin |
| 6,221,997 B1 | 4/2001 | Woodhouse et al. |
| 6,284,836 B1 | 9/2001 | Hassel et al. |
| 6,294,550 B1 | 9/2001 | Place et al. |
| 6,303,147 B1 | 10/2001 | Gilis |
| 6,303,606 B1 | 10/2001 | Leonardi et al. |
| 6,306,841 B1 | 10/2001 | Place et al. |
| 6,323,241 B1 | 11/2001 | Yeager et al. |
| 6,328,991 B1 | 12/2001 | Myhling |
| 6,335,003 B1 | 1/2002 | Kim et al. |
| 6,346,599 B1 | 2/2002 | Goldberg et al. |
| 6,359,100 B1 | 3/2002 | Hostettler et al. |
| 6,403,665 B1 | 6/2002 | Sieker et al. |
| 6,410,595 B1 | 6/2002 | Neal |
| 6,413,536 B1 | 7/2002 | Gibson et al. |
| 6,414,027 B1 | 7/2002 | Neal |
| 6,414,028 B1 | 7/2002 | Buyuktimkin et al. |
| 6,416,779 B1 | 7/2002 | D'Augustine et al. |
| 6,420,510 B1 | 7/2002 | Kaufhold et al. |
| 6,423,788 B1 | 7/2002 | Bammel et al. |
| 6,440,568 B1 | 8/2002 | Kayanoki et al. |
| 6,469,016 B1 | 10/2002 | Place et al. |
| 6,469,055 B2 | 10/2002 | Lee et al. |
| 6,471,955 B1 | 10/2002 | Tremont et al. |
| 6,472,434 B1 | 10/2002 | Place et al. |
| 6,482,345 B1 | 11/2002 | Dewanjee |
| 6,486,207 B2 | 11/2002 | Yeager et al. |
| 6,488,953 B2 | 12/2002 | Halliday et al. |
| 6,495,157 B1 | 12/2002 | Pena et al. |
| 6,511,388 B1 | 1/2003 | Dewanjee |
| 6,512,073 B2 | 1/2003 | Gertzmann et al. |
| 6,521,164 B1 | 2/2003 | Plummer et al. |
| 6,537,970 B1 | 3/2003 | Vulpescu et al. |
| 6,543,828 B1 | 4/2003 | Gass |
| 6,545,119 B2 | 4/2003 | Kizumoto et al. |
| 6,559,184 B2 | 5/2003 | Neal |
| 6,572,874 B1 | 6/2003 | Harrison et al. |
| 6,586,553 B1 | 7/2003 | Muhlfeld et al. |
| 6,589,990 B1 | 7/2003 | Kanakaris et al. |
| 6,592,472 B2 | 7/2003 | Dewanjee |
| 6,593,313 B2 | 7/2003 | Place et al. |
| 6,593,369 B2 | 7/2003 | Neal |
| 6,607,686 B2 | 8/2003 | Dewanjee |
| 6,630,050 B1 | 10/2003 | Moeller et al. |
| 6,632,913 B2 | 10/2003 | Matsumoto et al. |
| 6,641,064 B1 | 11/2003 | Dentler et al. |
| 6,642,274 B1 | 11/2003 | Neal |
| 6,664,290 B1 | 12/2003 | El-Rafaey |
| 6,693,135 B2 | 2/2004 | Yeager et al. |
| 6,740,333 B2 | 5/2004 | Beckett et al. |
| 6,790,926 B1 | 9/2004 | Spijkers et al. |
| 6,794,372 B2 | 9/2004 | Del Soldato et al. |
| 6,825,234 B2 | 11/2004 | Yeager et al. |
| 6,841,574 B2 | 1/2005 | Mo et al. |
| 6,861,503 B2 | 3/2005 | Shalaby |
| 6,953,800 B2 | 10/2005 | Leonardi et al. |
| 6,992,161 B1 | 1/2006 | Kim et al. |
| 7,053,209 B1 | 5/2006 | Gibson et al. |
| 7,179,481 B2 | 2/2007 | Villanueva |
| 7,485,666 B2 | 2/2009 | Villanueva et al. |
| 7,670,606 B2 | 3/2010 | Volkmann |
| 7,717,892 B2 | 5/2010 | Bartning |
| 7,795,467 B1 | 9/2010 | Pacetti et al. |
| 7,829,112 B2 | 11/2010 | Ron et al. |
| 7,833,543 B2 | 11/2010 | Gibson et al. |
| 7,833,545 B2 | 11/2010 | Ron et al. |
| 7,838,024 B2 | 11/2010 | Ron et al. |
| 7,883,718 B2 | 2/2011 | Ron et al. |
| 7,892,163 B2 | 2/2011 | Bartning et al. |
| 2001/0014715 A1 | 8/2001 | Blum et al. |
| 2001/0044467 A1 | 11/2001 | Neal |
| 2001/0051656 A1 | 12/2001 | Place et al. |
| 2001/0051694 A1 | 12/2001 | Barges et al. |
| 2002/0004529 A1 | 1/2002 | Neal |
| 2002/0013304 A1 | 1/2002 | Wilson et al. |
| 2002/0028846 A1 | 3/2002 | Yeager et al. |
| 2002/0037491 A1 | 3/2002 | Halliday et al. |
| 2002/0039935 A1 | 4/2002 | Dewanjee |
| 2002/0045665 A1 | 4/2002 | Yeager et al. |
| 2002/0052407 A1 | 5/2002 | Lee et al. |
| 2002/0062097 A1 | 5/2002 | Simpson |
| 2002/0077442 A1 | 6/2002 | Gertzmann et al. |
| 2002/0077444 A1 | 6/2002 | Matsumoto et al. |
| 2002/0099003 A1 | 7/2002 | Wilson et al. |
| 2002/0115814 A1 | 8/2002 | Woodhouse et al. |
| 2002/0115976 A1 | 8/2002 | Fleming |
| 2002/0119833 A1 | 8/2002 | Dewanjee |
| 2002/0128314 A1 | 9/2002 | Neal |
| 2002/0132965 A1 | 9/2002 | Gertzmann et al. |
| 2002/0161009 A1 | 10/2002 | Leonardi et al. |
| 2003/0022022 A1 | 1/2003 | Kizumoto et al. |
| 2003/0032754 A1 | 2/2003 | Kaufhold et al. |
| 2003/0032759 A1 | 2/2003 | Fischer et al. |
| 2003/0045668 A1 | 3/2003 | Fischer et al. |
| 2003/0060589 A1 | 3/2003 | Shimizu et al. |
| 2003/0122282 A1 | 7/2003 | Plummer et al. |
| 2003/0129241 A1 | 7/2003 | Yeager et al. |
| 2003/0134903 A1 | 7/2003 | Yeager et al. |
| 2003/0144454 A1 | 7/2003 | Krebs et al. |
| 2003/0158369 A1 | 8/2003 | Slagel |
| 2003/0207852 A1 | 11/2003 | Place et al. |
| 2003/0212139 A1 | 11/2003 | Neal |
| 2004/0014761 A1 | 1/2004 | Place et al. |
| 2004/0044080 A1 | 3/2004 | Place et al. |
| 2004/0047910 A1 | 3/2004 | Beckett et al. |
| 2004/0110843 A1 | 6/2004 | Yeager et al. |
| 2004/0115229 A1 | 6/2004 | Roby |
| 2004/0131664 A1 | 7/2004 | Mo et al. |
| 2004/0142847 A1 | 7/2004 | Bayersdoerfer et al. |
| 2004/0157766 A1 | 8/2004 | Embil et al. |
| 2004/0265355 A1 | 12/2004 | Shalaby |
| 2004/0266688 A1 | 12/2004 | Nayak |
| 2005/0004226 A1 | 1/2005 | Lu et al. |
| 2005/0013793 A1 | 1/2005 | Beckman et al. |
| 2005/0031690 A1 | 2/2005 | Rohrs et al. |
| 2005/0048104 A1 | 3/2005 | Venkatraman et al. |
| 2005/0053639 A1 | 3/2005 | Shalaby |
| 2005/0053670 A1 | 3/2005 | Schaub |
| 2005/0070516 A1 | 3/2005 | Wilson et al. |
| 2005/0090474 A1 | 4/2005 | Naor |
| 2005/0095245 A1 | 5/2005 | Riley et al. |
| 2005/0161030 A1 | 7/2005 | Roberts et al. |
| 2005/0169975 A1 | 8/2005 | Suzuki et al. |
| 2005/0181030 A1 | 8/2005 | Mo et al. |
| 2005/0187342 A1 | 8/2005 | Schieferstein et al. |
| 2005/0208152 A1 | 9/2005 | Milankovits |
| 2005/0238722 A1 | 10/2005 | Pathak et al. |
| 2005/0245902 A1 | 11/2005 | Cornish et al. |
| 2006/0003950 A1 | 1/2006 | Strugnell et al. |
| 2006/0018951 A1 | 1/2006 | Maniar et al. |
| 2006/0041021 A1 | 2/2006 | Wilson et al. |
| 2006/0052341 A1 | 3/2006 | Cornish et al. |

(56) References Cited

U.S. PATENT DOCUMENTS

| | | | |
|---|---|---|---|
| 2006/0078616 A1 | 4/2006 | Georgewill et al. |
| 2006/0093675 A1 | 5/2006 | Ebmeier et al. |
| 2006/0134161 A1 | 6/2006 | Halliday |
| 2006/0183724 A1 | 8/2006 | Diliberti et al. |
| 2006/0210599 A1 | 9/2006 | Gibson et al. |
| 2007/0043332 A1 | 2/2007 | Malcolm et al. |
| 2007/0128154 A1 | 6/2007 | Hadba et al. |
| 2007/0135605 A1 | 6/2007 | Hadba et al. |
| 2007/0148105 A1 | 6/2007 | Spector |
| 2007/0155906 A1 | 7/2007 | Hissink et al. |
| 2007/0166382 A1 | 7/2007 | Kiser et al. |
| 2007/0282093 A1 | 12/2007 | Yoshimura et al. |
| 2008/0009663 A1 | 1/2008 | Bartning et al. |
| 2008/0009666 A1 | 1/2008 | Bartning et al. |
| 2008/0108775 A1 | 5/2008 | Schieferstein et al. |
| 2008/0140185 A1 | 6/2008 | Kiser et al. |
| 2008/0145419 A1 | 6/2008 | Gibson et al. |
| 2008/0152708 A1 | 6/2008 | Gibson et al. |
| 2008/0199511 A1 | 8/2008 | Sitruk-Ware et al. |
| 2008/0206310 A1 | 8/2008 | Davis |
| 2008/0207571 A1 | 8/2008 | Davis |
| 2008/0262613 A1 | 10/2008 | Gogolewski |
| 2008/0271190 A1 | 10/2008 | Holland |
| 2008/0286339 A1 | 11/2008 | Ron et al. |
| 2009/0004246 A1 | 1/2009 | Woolfson et al. |
| 2009/0011209 A1 | 1/2009 | Steinberger et al. |
| 2009/0060982 A1 | 3/2009 | Ron et al. |
| 2009/0061172 A1 | 3/2009 | Hayashi et al. |
| 2009/0081278 A1 | 3/2009 | De Graaff et al. |
| 2009/0203591 A1 | 8/2009 | Bagchi et al. |
| 2009/0203772 A1 | 8/2009 | Villanueva et al. |
| 2009/0291120 A1 | 11/2009 | Tuominen et al. |
| 2010/0104619 A1 | 4/2010 | De Graaff et al. |
| 2010/0203104 A1 | 8/2010 | De Graaff et al. |
| 2010/0285094 A1 | 11/2010 | Gupta |
| 2011/0045076 A1 | 2/2011 | Kiser et al. |
| 2011/0056501 A1 | 3/2011 | Kortesuo et al. |
| 2011/0059040 A1 | 3/2011 | Kiser et al. |
| 2011/0077578 A1 | 3/2011 | Bartning et al. |
| 2011/0091488 A1 | 4/2011 | Halliday et al. |
| 2011/0150955 A1 | 6/2011 | Klingman |

FOREIGN PATENT DOCUMENTS

| | | | |
|---|---|---|---|
| EP | 335669 | 3/1989 | |
| EP | 0401990 | 5/1990 | |
| EP | 424164 | 10/1990 | |
| EP | 0401990 | 12/1990 | |
| EP | 450176 | 10/1991 | |
| EP | 0456176 | 10/1991 | |
| EP | 10/35837 | 4/2003 | |
| EP | 1063942 | 6/2004 | |
| FR | 2557576 | 7/1985 | |
| FR | 2705567 | 12/1994 | |
| GB | 2047093 | 11/1980 | |
| GB | 2047094 | 11/1980 | |
| GB | 2244920 | 12/1991 | |
| JP | 56500253 | 3/1980 | |
| JP | 1135488 | 9/1989 | |
| JP | 1150610 | 10/1989 | |
| JP | 0670952 | 3/1994 | |
| JP | 200502691 | 3/2000 | |
| JP | 2001513550 | 9/2001 | |
| JP | 2002515069 | 5/2002 | |
| JP | 2011/507405 | 3/2011 | |
| WO | WO 80/01984 | 10/1980 | |
| WO | 8905319 | 6/1989 | |
| WO | 8907117 | 8/1989 | |
| WO | 9102763 | 3/1991 | |
| WO | 9403510 | 2/1994 | |
| WO | 9413724 | 6/1994 | |
| WO | 9422934 | 10/1994 | |
| WO | 9606875 | 3/1996 | |
| WO | 9615171 | 5/1996 | |
| WO | 9621427 | 7/1996 | |
| WO | 96/31551 | 10/1996 | |
| WO | WO 96/38153 | 12/1996 | |
| WO | 9717386 | 5/1997 | |
| WO | 9724109 | 7/1997 | |
| WO | WO 97/24109 | 7/1997 | |
| WO | WO 98/56323 | 12/1998 | |
| WO | WO 99/09964 | 3/1999 | |
| WO | 9947073 | 9/1999 | |
| WO | 9947127 | 9/1999 | |
| WO | 9956731 | 11/1999 | |
| WO | 0000222 | 1/2000 | |
| WO | 0040222 | 7/2000 | |
| WO | WO 00/40222 | 7/2000 | |
| WO | WO 02/03896 | 1/2002 | |
| WO | WO 02/09631 | 2/2002 | |
| WO | 03011301 | 2/2003 | |
| WO | 03087183 | 10/2003 | |
| WO | 2004/029125 | 4/2004 | |
| WO | WO2004029125 | * 4/2004 | ............ C08G 18/48 |
| WO | 2004004872 | 10/2004 | |
| WO | 2005068533 | 7/2005 | |
| WO | WO 2005/063145 | 7/2005 | |
| WO | 2005089778 | 9/2005 | |
| WO | 2005116100 | 12/2005 | |
| WO | 2006013335 | 2/2006 | |
| WO | 2006048639 | 5/2006 | |
| WO | 2006048639 | 11/2006 | |
| WO | 2008007098 | 1/2008 | |
| WO | 2009094573 | 7/2009 | |
| WO | WO 2010/119029 | 5/2010 | |
| WO | WO 2011/011099 | 1/2011 | |
| WO | WO 2011/039418 | 4/2011 | |

OTHER PUBLICATIONS

PCT/GB2007/002401 Written Opinion of the International Searching Authority dated Oct. 24, 2007.

Casteneda, C.S., et al. "Misoprostol Dose Selection in a Controlled-Release Vaginal Insert for Induction of Labor in Nulliparous Women," American Journal of Obstetrics and Gynecology, 193:1071-1075, (Sep. 2005).

Tyagi, P., et al. "Sustained Intravesical Drug Delivery Using Thermosensitive Hydrogel," Pharmaceutical Research, 21 (5):832-837 (May 2004).

Abraham, Gustavo A., et al. "Bioresorbable poly(ester-ether urethane)s from L-lysine diisocyanate and triblock copolymers with different hydrophilic character," Wiley Periodicals 2005.

Yu, J., et al. "Blood interactions with novel polyurethaneurea hydrogels," Biomaterials 12(2): 119-120 (1991).

PCT/GB2003/004208 International Search Report dated Jan. 2, 2004.

PCT/GB2007/002415 International Search Report dated Oct. 30, 2007.

PCT/GB2007/002415 Written Opinion of the International Searching Authority dated Oct. 30, 2007.

PCT/GB2005/002951 Written Opinion of the International Searching Authority dated Oct. 6, 2005.

PCT/GB2005/002951 International Preliminary Report on Patentability dated Feb. 6, 2007.

PCT/GB2005/002951 International Search Report dated Oct. 20, 2005.

PCTGB207 002604 International Search Report Jul. 12, 2007.

PCTGB207 002604 Written Opinion of International Searching Authority Jul. 12, 2007.

Chen, "Stabilization and sustained-release effect of Misoprostol with Methacrylate copolymer", International Journal of Pharmaceutics, 203 (2000) pp. 141-148.

Kararli, "Stabilization of Misoprostol with Hydroxypropyl Methylcellulose (HMPC) Against Degradation by Water", Pharmaceutical Research, vol. 7, No. 11 (1990).

PCT/GB2007/002604, International Search Report, dated Jul. 12, 2007.

Merck Index (Ninth Edition, 1976, p. 4073).

(56) References Cited

OTHER PUBLICATIONS

Santerre, et al., "Understanding the biodegradation of polyurethanes: From classical implants to tissue engineering materials." Biomaterials 26(35), Dec. 2005: 7457-7470.

Leiva et al., "Poly(£-caprolactone)-block-poly(ethylene-oxide)-block-poly(£-V caprolactone): Biodegradable triblock copolymer spread at the air-water interface." European Polymer Journal 44(8), Aug. 2008:2589-2598.

Zhou et al., "Biodegradable poly(e-caprolactone)-poly(ethylene glycol) block copolymers: characterization and their use as drug carriers for a controlled delivery system." Biomaterials (2003) 24(20): 3563-3570.

Jianzhong et al. "Polycaprolactone-poly(ethylene glycol) block copolymer III Drug release behavior." Chinese J Polym Sci., 13(2) 1995:154:161.

Lee JW, et al., "Thermoreversible gelation of biodegradable poly(epsilon-caprolactone) and poly(ethylene glycol)multiblock copolymers in aqueous solutions." J Control Release. Jun. 15, 2001; 73(2-3):315-27.

Abraham, et al., "Bioresorbable poly(ester-ether urethane)s from L-lysine diisocyanate and triblock copolymers with different hydrophilic character." Journal of Biomedical Materials Research Part A (2006) 76(4): 729-736.

Baimak et al., "Synthesis and characterization of poly(I-lactide-co-e-caprolactone) copolymers: Effect of stannous octoate initiator and diethylel glycol coinitiator concentration." ScienceAsia 30 (2004):324-334.

* cited by examiner

Figure 1. Molecular weight analysis as a function of polymerization time for Polymer A Figure 2. Comparison of the fluconazole release profiles from the crosslinked polymer, linear high-swelling polymers, polymer A and polymer E.

HYDROPHILIC POLYURETHANE COMPOSITIONS

This application is a national stage filing under 35 U.S.C. §371 of International Application PCT/GB2007/002401, filed Jun. 27, 2007, which claims priority from United Kingdom Application GB 0613333.4, filed Jul. 5, 2006, the entireties of each of which are hereby incorporated by reference. International Application PCT/GB2007/002401 was published under PCT Article 21(2) in English.

The present invention relates to hydrophilic linear polyurethane polymers, suitable for the production of controlled release compositions for release of pharmaceutically active agents over a prolonged period of time.

Certain cross-linked polyurethane hydrogel polymers are known from European Patent Publication EP0016652 and EP0016654. These patent specifications describe cross-linked polyurethanes formed by reacting a polyethylene oxide of equivalent weight greater than 1500 with a polyfunctional isocyanate and a trifunctional compound reactive therewith, such as an alkane triol. The resultant cross-linked polyurethane polymers are water-swellable to form a hydrogel but are water-insoluble and may be loaded with water-soluble pharmaceutically active agents. One particular polyurethane polymer is the reaction product of polyethylene glycol (PEG) 8000, dicyclohexylmethane-4,4-diisocyanate (DMDI) and 1,2,6-hexane triol and which has been used commercially for vaginal delivery of prostaglandins.

However, such cross-linked polyurethane polymers possess a number of practical disadvantages. Whilst the use of a triol cross-linking agent is effective in providing polymers of relatively reproducible swelling characteristics, the percent swelling is typically 200-300% (i.e. the increase in weight of the swollen polymer divided by the weight of the dry polymer). Pharmaceutically active agents are loaded by contacting the polymer with an aqueous solution of pharmaceutically active agent, such that the solution becomes absorbed into the polymer, forming a hydrogel. The swollen polymer is then dried back to a chosen water content before use. As a consequence, the degree of swelling limits the molecular weight of the pharmaceutically active agent which can be absorbed into the hydrogel structure to below about 3000 g/mol. A further disadvantage is that only water-soluble pharmaceutically active agents may be used for loading. And the release properties are quite limited since prolonged release cannot be achieved; a maximum release time of 24 hours in vivo can be attained for water soluble drugs.

In addition to these disadvantages, the conventional cross-linked polyurethane polymer is essentially a non-thermoplastic polymer (thermoset), and is therefore insoluble in both water and organic solvents, making the further processing of the polymer into other solid forms, such as films, monolithic devices, foams, wafers, composites, sandwich structures, particles, pellets, foams or coatings, effectively impossible. In addition, the thermoset nature of the conventional cross-linked polyurethane polymer excludes the possibility of melt mixing drug and polymer in order to load the polymer with a suitable active agent without using solvents or water.

Certain thermoplastic polyurethane hydrogel polymers are known from patent Publication WO2004029125 (PCT/GB2003/004208). This patent specification describes linear thermoplastic polyurethanes formed by reacting a polyethylene oxide of molecular weight of greater than 4000 g/mol with a polyfunctional isocyanate and a bifunctional compound reactive therewith, such as an alkane diol or diamine. The resultant thermoplastic polyurethane polymers are water-swellable to form a hydrogel but are water-insoluble and may be loaded with water-soluble pharmaceutically active agents. One particular polyurethane polymer is the reaction product of polyethylene glycol 8000, Desmodur (DMDI i.e. dicyclohexylmethane-4,4-diisocyanate) and 1,10 decane diol, which has shown %-swelling from 600 up to 1700% or even above. This type of polymer has shown its suitability for diffusion loading and short-term delivery of relatively water-soluble drugs e.g. Clindamycin phosphate, Oxytocin, and Misoprostol.

However, such high-swelling thermoplastic polyurethane polymers also possess some practical disadvantages. Due to the high weight content and block length of PEG, the polymer is only suitable for relatively short-term release (i.e. controlled release from 10 min to only a few hours) of active agents, especially in the case of highly water-soluble drugs. In addition, the low hydrophobic content, e.g. low amount of hydrophobic compound e.g. decane diol (DD) or dodecanediol (DDD), makes the polymer inappropriate for hydrophobic drugs; thus restricting its use. Furthermore, this imbalance between hydrophobic and hydrophilic regions hampers the microphase separation, reducing the mechanical strength of the polymer in both dry and wet states. Hydrophilic and hydrophobic drugs need to have interactions with both of the phases in order for their release to be controlled by the polymer structure.

The swelling percentage of high-swelling thermoplastic polyurethanes is typically 200-1700% and is dependent on the PEG content and/or the length of PEG block. Pharmaceutically active agents can be loaded by using exactly the same method as the one described above for the conventional cross-linked polyurethane, and the release times and profiles are very similar.

Patent specification WO 94/22934 discloses the production of a linear random block copolymer from polyethylene oxide (number average molecular weight 1000 to 12,000), a diamine and a diisocyanate. Yu et al. Biomaterials 12 (1991) March, No. 2, page 119-120 discloses the use of polyurethane hydrogels formed of polyethylene glycol (number average molecular weight of 5830) and a low molecular weight polypropylene glycol (molecular weight 425) and a diisocyanate. Patent specification U.S. Pat. No. 4,202,880 discloses the production of polyurethanes from polyethylene glycol (molecular weight 400-20,000), an alkaline glycol containing from 2-6 carbon atoms and a diisocyanate. Patent specification U.S. Pat. No. 4,235,988 is a similar disclosure, although the preferred PEG range is 600-6,000.

An object of certain embodiments of the present invention is to provide a hydrophilic, low-swelling, linear polyurethane polymer of the aforementioned type. Another object is to enhance the processability of the polymer to allow the use of conventional melt processing techniques e.g. extrusion, compression moulding and injection moulding, as well as different type of solvents in the polymer processing and drug loading steps.

The present invention is based on the synthesis of low-swelling linear polyurethanes having suitable melt processing properties for drug loading, as well as good drug release characteristics, which are prepared by reacting a polyethylene glycol with a diol or other difunctional compound and a difunctional isocyanate.

In particular, the present invention provides a water-swellable linear polymer obtainable by reacting together:
  a polyethylene oxide of number average molecular weight less than 4000;
  an aliphatic diol; and
  a difunctional isocyanate The linear low-swelling polymer produced is swellable in water to a certain degree, depending upon the ratio of the three components (a), (b) and (c), for example from 1% up to 200% (e.g. 20 to 100%), thus obtaining better control over the release of pharmaceutically active agents than from the known high-swelling linear polymer. The polymers of the invention may also swell in other solvents (in which they are insoluble) such as ethanol or isopropyl alcohol. The linear polymer of the present invention is also soluble in certain organic solvents, such as dichloromethane, 1-methyl-2-pyrrolidone (NMP) and tetrahydrofuran, which allows the polymer to be dissolved and cast into films or coatings. It also allows the loading of thermally unstable active agents with poor water solubility but which are soluble in organic solvents, to be loaded into the polymer.

Polyethylene oxides contain the repeating unit (—$CH_2CH_2O$—) and are conveniently prepared by the stepwise addition of ethylene oxide to a compound containing a reactive hydrogen atom. Polyethylene glycols are prepared by the addition of ethylene oxide to ethylene glycol to produce a difunctional polyethylene glycol structure $HO(CH_2CH_2O)_nH$ wherein n is an integer of varying size depending on the molecular weight of polyethylene oxide. Polyethylene oxides used in the present invention are generally linear polyethylene glycols i.e. diols having an molecular wt. weight of 200 to 4000 g/mol.

The difunctional aliphatic diol is reactive with the difunctional isocyanate, and is typically at least a $C_6$ or $C_8$ diol. Diols in the range $C_5$ to $C_{20}$, preferably $C_8$ to $C_{15}$ are preferred. Thus, decane diol has been found to produce particularly good results. The diol may be a saturated or unsaturated diol. Branched diols may be used but straight chain diols are preferred. The two hydroxy groups are generally on terminal carbon atoms. Thus, preferred diols include 1,6-hexanediol, 1,10-decanediol, 1,12-dodecanediol and 1,16-hexadecanediol.

The difunctional isocyanate is generally one of the conventional diisocyanates, such as dicyclohexylmethane-4,4-diisocyanate, diphenylmethane-4,4-diisocyanate, 1,6-hexamethylene diisocyanate etc.

The ratio of the components (a) to (b) to (c) (in terms of equivalent weights) is generally in the range 0.01-0.1 to 1 to 1.01-1.1. Of course, the skilled man through reasonable experimentation would determine the best ratio of ingredients to give the desired properties. The amount of component (c) is generally equal to the combined amounts of (a) and (b) to provide the correct stoichiometry.

Preferably, the amount of hydrophilic PEG units is less than 50 wt %, preferably less than 40 wt %, and often less than 30 wt %. Also, the amount of hydrophobic diol preferably exceeds 20 wt %, 30 wt % or 40 wt %. The diisocyanate is generally 20-50 wt % of the polymer.

The invention also provides a method of producing the polymer, which comprises melting and drying the polyethylene oxide together with the aliphatic diol at a temperature of 85° C. to 100° C. under vacuum; and then adding the difunctional isocyanate.

The polymers are generally produced by melting and drying polyethylene glycol together with the difunctional compound along with a typical polyurethane catalyst, e.g ferric chloride, triethylene diamine (DABCO) and/or tin(II) octoate, at a temperature of 85° to 100° C. (e.g. 95° C.) and under vacuum to remove excess moisture before the diisocyanate, e.g DMDI or HMDI is added thereto. The reaction mixture is then poured into moulds and reacted for a specified time. Thus, the polymer is initially formed as a solid. However, the linear polymers of the present invention are soluble in certain organic solvents such as those given in Table 2 (though not all polymers are soluble in all solvents). This allows the polymer to be dissolved and the resultant solution cast into films. The solution may also be employed for coating granules, tablets etc., in order to modify their release properties. Alternatively, the solution can be poured into a non-solvent so as to precipitate polymer/active microparticles. In addition, the polymer can be ground, chopped, pelletised and melted using conventional techniques for processing thermoplastic polymers.

Thus, the invention also provides controlled release compositions comprising the linear polymer together with an active agent. Any suitable type of plastic processing equipment, e.g extruder, injection moulding machine, and melt mixer can be used for mixing polymer and drug and forming or reshaping them into any type of drug loaded format. The active agent may be a pharmaceutically active agent for human or animal use. It may also be any other agent where sustained release properties (e.g. algicides, fertilisers etc.) are required. The pharmaceutical solid dosage forms include suppositories, rings and pessaries for vaginal use, buccal inserts for oral administration, patches for transdermal administration etc. These dosage forms are generally administered to the patient, retained in place until delivery of active agent has occurred and the polymer is then removed.

The polymer may also be used for implants, which remain in the body; or for coating such implants (e.g. stents).

The linear polymer of the present invention is an amphiphilic thermoplastic polymer and is thus suitable for the uptake of hydrophilic, hydrophobic, low and high molecular weight pharmaceutically active agents (up to and exceeding a molecular weight of 3000 e.g. 10,000, 50,000, 100,000 or even up to 200,000). Generally, the molecular weight of the active agent is in the range 200 to 20,000. A wide variety of water-soluble pharmaceutically active substances such as those listed in patent specification EP0016652 may thus be incorporated. Furthermore, the linear polymers of the present invention may be loaded with pharmaceutically active agents, which are poorly water-soluble, provided that these can be dissolved in a common solvent with the polymer. The resultant solution can then be cast into any desired solid forms. In addition, the linear polymers of the present invention may be extrusion loaded or melt mixed with pharmaceutically active agents, which are thermally stable at the polymer processing temperature.

The release time of the present polymers may exceed 200, 400, 800, 1200 mins or even longer—for substantially complete release of available active agent.

Pharmaceutically active agents of particular interest include:
Proteins e.g. interferon alpha, beta and gamma, insulin, human growth hormone, leuprolide; Benzodiazepines e.g. midazolam; Anti-migraine agents e.g. triptophans, ergotamine and its derivatives; Anti-infective agents e.g. azoles, bacterial vaginosis, candida; and opthalmic agents e.g. latanoprost.

A detailed list of active agent includes $H_2$ receptor antagonist, antimuscaririe, prostaglandin analogue, proton pump inhibitor, aminosalycilate, corticosteroid, chelating agent, cardiac glycoside, phosphodiesterase inhibitor, thiazide, diuretic, carbonic anhydrase inhibitor, antihypertensive, anticancer, anti-depressant, calcium channel blocker, analgesic, opioid antagonist, antiplatel, anticoagulant, fibrinolytic, statin, adrenoceptor agonist, beta blocker, antihistamine, respiratory stimulant, micolytic, expectorant, benzodiazepine, barbiturate, anxiolytic, antipsychotic, tricyclic antidepressant, $5HT_1$, antagonist, opiate, 5HT, agonist, antiemetic, antiepileptic, dopaminergic, antibiotic, antifungal, anthelmintic, antiviral, antiprotozoal, antidiabetic, insulin, thyrtoxin, female sex hormone, male sex hormone, antiestrogen, hypothalamic, pituitary hormone, posterior pituitary hormone antagonist, antidiuretic hormone antagonist, bisphosphonate, dopamine receptor stimulant, androgen, non-steroidal anti-inflammatory, immuno suppressant local anaesthetic, sedative, antipsoriatic, silver salt, topical antibacterial, vaccine.

Embodiments of the present invention will now be described by way of examples below. The effects of type and ratios of polyethylene glycols, diols and diisocyanates on the properties of polymers can be seen in the following Tables, Examples and Figures.

In the Figures.

EXAMPLE 1

Polymer Manufacture

Various types of polyethylene glycols, diols and diisocyanates, in a range of stoichiometric ratios were used to demonstrate their effect on the properties of the hydrophilic linear polyurethane polymers produced. PEG400, PEG600, PEG1000, PEG1200, PEG2000 and PEG4000 are polyethylene glycols having molecular weights of 400, 600, 1000, 1200, 2000 and 4000 g/mol, respectively; DD is 1,10-decanediol and DDD is 1,12-dodecanediol; DMDI is dicyclohexylmethane-4,4-diisocyanate and HMDI is 1,6-hexamethylene diisocyanate; FECl3 is Ferric chloride, DABCO is triethylene diamine; $SnOct_2$ is stannous octoate.

Polymers were produced using the polymerisation method in patent Publication WO2004029125. The PEG was melted and vacuum dried at 95° C. with diol and catalyst in a rota-evaporator, before diisocyanate addition. Table 1 shows the manufactured polymers which were produced.

EXAMPLE 2

Polymerisation Reaction as a Function of Time

Figure 1:
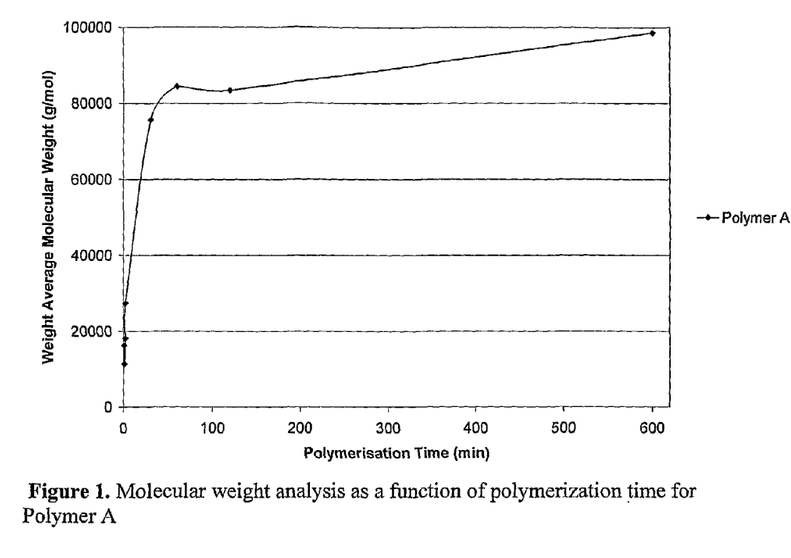
FIG. 1 shows variation of molecular weight with polymerisation time for polymer A.

The effect of polymerisation time on the polymer produced was investigated using triple detection Size Exclusion Chromatography (SEC). Molecular weight determination as a function of polymerisation time was carried out for Polymer A and is shown in FIG. 1. The molecular weight of the polymer will determine the rheology, melt flow and mechanical properties of the polymer. Therefore the importance of determining molecular weight values is evident.

EXAMPLE 3

The Effect of the Catalyst on the Polymerisation Reactions

The polymerisations were performed as in Example 1 but the ferric chloride was replaced by DABCO and $SnOct_2$ for Polymer P (Table 1); while DABCO alone was used for Polymer O (Table 1). Polymer D (Table 1) was prepared in the absence of a catalyst.

EXAMPLE 4

The Use of Different Diisocyanates

The polymerisations were performed as in Example 1 but the DMDI was replaced by HMDI for Polymers C, D, F, H, I, J, K, L. M, O and P in Table 1.

EXAMPLE 5

A Two Step Polymerisation Method

A two-step polymerisation method was used for making Polymer H in Table 1. The PEG-catalyst mixture was dried in a rotary-evaporator prior to the polymerization reaction. The diisocyanate (HMDI) was first fed to the heated (95° C.) stirring tank reactor followed by the addition of the molten

TABLE 1

Manufactured hydrophilic polyurethane polymers.

| | PEG | | | DD | | | DDD | | | DMDI | | | HMDI | | |
|---|---|---|---|---|---|---|---|---|---|---|---|---|---|---|---|
| Polymer Name | Mw | mol ratio | wt % | Mw | mol ratio | wt % | Mw | mol ratio | wt % | Mw | mol ratio | wt % | Mw | mol ratio | wt % |
| Polymer A | 4000 | 0.1 | 46.4 | 174 | 1 | 20.2 | — | — | — | 262 | 1.1 | 33.4 | — | — | — |
| Polymer B | 4000 | 0.1 | 44.9 | — | — | — | 202 | 1 | 22.7 | 262 | 1.1 | 32.4 | — | — | — |
| Polymer C | 4000 | 0.1 | 50.8 | — | — | — | 202 | 1 | 25.7 | — | — | — | 168 | 1.1 | 23.5 |
| Polymer D *1 | 4000 | 0.1 | 50.8 | — | — | — | 202 | 1 | 25.7 | — | — | — | 168 | 1.1 | 23.5 |
| Polymer E | 4000 | 0.05 | 29.5 | — | — | — | 202 | 1 | 29.8 | 262 | 1.05 | 40.6 | — | — | — |
| Polymer F | 4000 | 0.05 | 34.6 | — | — | — | 202 | 1 | 34.9 | — | — | — | 168 | 1.05 | 30.5 |
| Polymer G | 4000 | 0.01 | 7.9 | — | — | — | 202 | 1 | 39.9 | 262 | 1.01 | 52.2 | — | — | — |
| Polymer H | 2000 | 0.1 | 34.1 | — | — | — | 202 | 1 | 34.4 | — | — | — | 168 | 1.1 | 31.5 |
| Polymer I | 2000 | 0.1 | 34.1 | — | — | — | 202 | 1 | 34.4 | — | — | — | 168 | 1.1 | 31.5 |
| Polymer J | 2000 | 0.05 | 20.9 | — | — | — | 202 | 1 | 42.2 | — | — | — | 168 | 1.05 | 36.9 |
| Polymer K | 1500 | 0.1 | 29.5 | 174 | 1 | 34.2 | — | — | — | — | — | — | 168 | 1.1 | 36.3 |
| Polymer L | 1500 | 0.05 | 17.6 | 174 | 1 | 40.9 | — | — | — | — | — | — | 168 | 1.05 | 41.5 |
| Polymer M | 400 | 0.1 | 10.0 | 174 | 1 | 43.6 | — | — | — | — | — | — | 168 | 1.1 | 46.3 |
| Polymer N | 400 | 0.1 | 8.0 | 174 | 1 | 34.7 | — | — | — | 262 | 1.1 | 57.4 | — | — | — |
| Polymer O *2 | 400 | 0.1 | 10.0 | 174 | 1 | 43.6 | — | — | — | — | — | — | 168 | 1.1 | 46.3 |
| Polymer P *3 | 400 | 0.1 | 10.0 | 174 | 1 | 43.6 | — | — | — | — | — | — | 168 | 1.1 | 46.3 |

*1 no catalyst
*2 DABCO
*3 DABCO + SnOct

PEG-catalyst mixture which was added in 12 minutes using a constant mixing (60 rpm). The reaction was allowed to continue for 28 more minutes at which point the diol (DDD) was fed to the reactor. The reaction mixture was stirred for 7 more minutes. At this point the mixing was stopped and the polymer was further cured for 10 hours at 95° C. before it was left to cool down to room temperature.

EXAMPLE 6

Solubility of Polymers in Different Solvents

A number of polymers from Table 1 were dissolved in different solvents in order to find suitable solvents. The solubility tests were carried out for 24 hours at room temperature (RT) or at elevated temperatures. The solubility results for the selected polymers are shown in Table 2.

TABLE 2

Polymer solubility in selected solvents and at different temperatures.

| Polymer Name | DCM RT | HFIP 40° C. | CHCl₃ 50° C. | THF 37° C. | DMAC 80° C. | DMSO 80° C. | NMP 85° C. | NMP 120° C. | NMP + LiBr 120° C. |
|---|---|---|---|---|---|---|---|---|---|
| Polymer A | YES | N/A | N/A | YES | N/A | N/A | N/A | N/A | N/A |
| Polymer B | YES | N/A | N/A | YES | N/A | N/A | N/A | N/A | N/A |
| Polymer C | NO | Gel | NO | NO | NO | NO | YES | N/A | N/A |
| Polymer D | NO | Gel | NO | NO | NO | NO | YES | N/A | N/A |
| Polymer E | YES | N/A | N/A | YES | N/A | N/A | N/A | N/A | N/A |
| Polymer F | NO | Gel | NO | NO | NO | NO | Gel | YES | YES |
| Polymer G | NO | N/A | YES | NO | YES | NO | YES | N/A | N/A |
| Polymer H | NO | Gel | NO | NO | NO | NO | YES | N/A | N/A |
| Polymer I | NO | Gel | NO | NO | NO | NO | YES | N/A | N/A |
| Polymer J | NO | Gel | NO | NO | NO | NO | Gel | Gel | YES |
| Polymer K | NO | YES | NO | NO | NO | NO | NO | YES | YES |
| Polymer L | NO | Gel | NO | NO | NO | NO | Gel | YES | YES |
| Polymer M | NO | Gel | NO | NO | NO | NO | Gel | YES | YES |
| Polymer N | YES | N/A | YES | YES | YES | NO | YES | N/A | N/A |
| Polymer O | NO | Gel | NO | NO | NO | NO | Gel | YES | YES |
| Polymer P | NO | Gel | NO | NO | NO | NO | Gel | YES | YES |

DCM dichloromethane
HFIP hexafluoro isopropanol
CHCl3 trichloromethane
THF tetrahydrofuran
DMAC dimethyl acetamide
DMSO dimethyl sulphoxide
NMP 1-methyl-2-pyrrolidone
LiBr lithium bromide

EXAMPLE 7

Swelling Capacity of Polymers in Different Solvents

The swelling determinations for a number of selected polymers were carried out in water, ethanol, isopropyl alcohol (IPA) and in a 50% mixture of IPA/water in order to measure the amount of solvent absorbed by the polymer. The results were calculated based on the average swelling of 5-10 specimens and are shown in Table 3. The formula used for the calculations is shown below:

$$\% \text{ Swelling} = \frac{\text{Swollen Weight} - \text{Dry Weight}}{\text{Dry Weight}} \times 100$$

TABLE 3

Percent swelling of the selected polymers in different swelling media (water, ethanol, IPA and 50% IPA/water).

| Polymer Name | % Swelling in Water | % Swelling in Ethanol | % Swelling in IPA | % Swelling in 50% IPA/water |
|---|---|---|---|---|
| Polymer A | 81 | 190 | 15 | 300 |
| Polymer E | 41 | 80 | 18 | 115 |
| Polymer J | 10 | — | — | — |
| Polymer K | 5.6 | — | — | — |
| Polymer P*3 | 1.5 | — | — | — |

EXAMPLE 8

Shore Hardness Testing

The manufactured polymers were tested for shore hardness using durometers A and D. These measurements are well known to the skilled in the field. The results are presented as the average of four measurements and are presented in Table 4.

TABLE 4

Shore hardness values determined for the manufactured polymers.

| | Durometer A | | Durometer D | |
|---|---|---|---|---|
| Polymer Name | Max Hardness | Creep (15 sec) | Max Hardness | Creep (15 sec) |
| Polymer A | 95.3 | 0.8 | 59.3 | 5.3 |
| Polymer B | 98.0 | 0.0 | 60.6 | 4.1 |
| Polymer C | 97.5 | 0.5 | 53.1 | 2.1 |
| Polymer D | 96.0 | 0.0 | 50.5 | 4.3 |

TABLE 4-continued

Shore hardness values determined for the manufactured polymers.

| Polymer Name | Durometer A | | Durometer D | |
|---|---|---|---|---|
| | Max Hardness | Creep (15 sec) | Max Hardness | Creep (15 sec) |
| Polymer E | 98.0 | 0.0 | 67.0 | 6.5 |
| Polymer F | 94.5 | 0.0 | 53.5 | 3.3 |
| Polymer G | 97.5 | 0.0 | 65.8 | 6.0 |
| Polymer H | N/A | N/A | N/A | N/A |
| Polymer I | 96.5 | 1.0 | 53.8 | 0.8 |
| Polymer J | 93.0 | 1.5 | 55.8 | 2.3 |
| Polymer K | 99.0 | 0.0 | 63.0 | 3.6 |
| Polymer L | 99.0 | 0.0 | 66.0 | 4.8 |
| Polymer M | 99.0 | 0.0 | 68.4 | 4.9 |
| Polymer N | 99.5 | 0.0 | 77.8 | 4.9 |
| Polymer O | 99.0 | 0.0 | 70.6 | 2.9 |
| Polymer P | 100.0 | 0.0 | 67.8 | 3.8 |

Experimental Conditions:
Temperature 21° C.
Relative Humidity % RH 39

EXAMPLE 9

Polymer Films Manufactured by Compression Moulding

A number of selected polymers and a drug loaded polymer formulation from Table 1 were dried over night under vacuum prior to the processing. The upper and lower plate temperatures of the compression moulding machine were set at the target processing temperature. Two Teflon sheets were placed between the mould and the hot plates. The melting time was 3-5 minutes followed by a 30-120 seconds holding under pressure (170-200 bars). A predetermined amount of polymer was used to fill the mould. After cooling to room temperature the samples (pessary devices with dimensions 30 mm×10 mm×1 mm) were mechanically punched out and kept in the freezer for further analysis. The film processing conditions are shown in Table 5.

TABLE 5

Thermal processing of the manufactured polymers using compression moulding.

| Polymer | Fluconazole (wt %) | Temperature (° C.) | Cylinder Pressure (Bar) | Melting Time (s) | Pressure Time (s) | Mould Thickness (mm) |
|---|---|---|---|---|---|---|
| Polymer A | — | 150 | 200 | 180 | 60 | 0.4 |
| Polymer B | — | 160 | 170 | 180 | 30 | 1.0 |
| Polymer B | — | 160 | 200 | 240 | 120 | 1.0 |
| Polymer C | — | 190 | 200 | 180 | 20 | 0.4 |
| Polymer C | — | 200 | 200 | 180 | 60 | 0.4 |
| Polymer D | — | 180 | 200 | 300 | 60 | 0.4 |
| Polymer D | — | 200 | 200 | 180 | 50 | 0.4 |
| Polymer E | — | 165 | 200 | 270 | 60 | 0.4 |
| Polymer E | 20 | 160 | 200 | 270 | 60 | 1.0 |
| Polymer E | — | 170 | 200 | 210 | 60 | 0.4 |
| Polymer H | — | 160 | 170 | 180 | 30 | 1.0 |
| Polymer P | — | 200 | 200 | 180 | 50 | 0.4 |

EXAMPLE 10

Drug Loading—Extrusion

Selected polymers were loaded with the model drug fluconazole. A 16 mm co-rotating twin-screw laboratory extruder was used for loading the polymers. Table 6 shows the drug loading conditions.

TABLE 6

Extrusion loading conditions used for the fluconazole loaded devices.

| Polymer | Drug | Drug (wt %) | Screw speed (rpm) | Temperature profile from feed to die (° C.) |
|---|---|---|---|---|
| Polymer A | Fluconazole | 20 | 30 | 96-150-150-150-155 |
| Polymer E | Fluconazole | 20 | 30 | 95-135-135-135-135 |

EXAMPLE 11

Drug Release Studies

Figure 2:
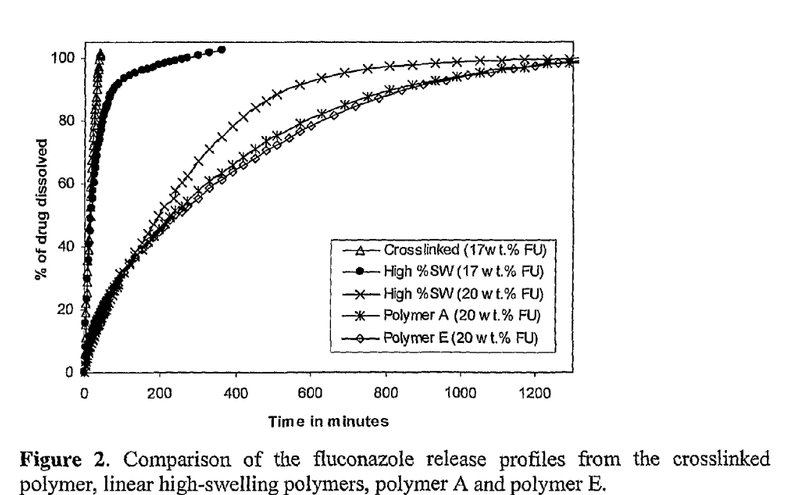
FIG. 2 is a comparison of release profiles for various polymers.

The amount of fluconazole released from the extrusion loaded polymers was investigated by a dissolution method based on the USP paddle method. This technique is comprised of an automated UV dissolution system where a Distek (2100C model) dissolution paddle (speed 50 rpm) is connected to a Unicam UV 500 spectrophotometer via an Icalis peristaltic pump. The system is operated using Dsolve software.
Experimental Conditions:
Temperature 37° C.
Dissolution media 500 ml of deionised degassed water In vitro drug release properties of the extrusion loaded polymers were compared with the diffusion loaded crosslinked and linear high swelling polymers, see FIG. 2. Extrusion loaded polymers A and E were plotted with another extrusion loaded linear high swelling polymer from patent WO2004029125 (high % SW 20 wt % fluconazole). The diffusion loaded crosslinked polymer from patent EP0016652/EP0016654 (crosslinked 17 wt % fluconazole) is also shown in the graph below along with another linear diffusion loaded high swelling polymer from patent WO2004029125 (high % SW 17 wt % fluconazole).

The invention claimed is
1. A controlled-release composition, comprising:
a water-swellable linear polymer together with an active agent, the water-swellable linear polymer obtained by reacting together:
(a) a polyethylene oxide of number average molecular weight less than or equal to 4000 g/mol;
(b) a $C_8$ to $C_{15}$ aliphatic diol; and
(c) a difunctional isocyanate,
wherein the ratio of components (a) to (b) to (c) is in the range of 0.01-0.1 to 1 to 1.01-1.1 in terms of equivalent weights, the amount of the polyethylene oxide is less than 50 wt % of the polymer, the polymer has a water swelling percentage of 20-100%, and the composition is in a solid dosage form.

2. The composition of claim 1, wherein the polyethylene oxide is a diol of molecular weight 200 to 4000 g/mol.

3. The composition of claim 1, wherein the aliphatic diol is 1,10-decanediol or 1,12-dodecanediol.

4. The composition of claim 1, wherein the difunctional isocyanate is dicyclohexylmethane-4.4-diisocyanate, diphenylmethane-4,4-diisocyanate, or 1,6-hexamethylene diisocyanate.

5. The composition of claim 1, wherein the amount of the aliphatic diol exceeds 20 wt % of the polymer.

6. The composition of claim 1, wherein the amount of the difunctional isocyanate is 20-50 wt % of the polymer.

7. The composition of claim 1, wherein the dosage form is a suppository, vaginal ring or pessary, a bucchal insert, or a transdermal patch.

8. The composition of claim 1, wherein the dosage form is an implant.

9. The composition of claim 1, wherein the active agent is a pharmaceutically active agent of molecular weight in the range 200 to 20,000 g/mol.

10. The composition of claim 1, wherein:
  (a) is a polyethylene glycol having a molecular weight of 4000 g/mol;
  (b) is 1,10-decanediol; and
  (c) is dicyclohexylmethane-4,4-diisocyanate.

11. The composition of claim 1, wherein the amount of the polyethylene oxide is less than 30 wt % of the polymer.

12. A method of producing the composition of claim 1, comprising melting and drying the polyethylene oxide together with the aliphatic diol at a temperature of 85° C. to 100° C. under vacuum; and then adding the difunctional isocyanate.

* * * * *